(12) United States Patent
Zak, III et al.

(10) Patent No.: US 11,458,039 B2
(45) Date of Patent: Oct. 4, 2022

(54) SYSTEM AND METHOD FOR TREATING BRAIN INJURY

(71) Applicant: TecTraum, Inc., Chagrin Falls, OH (US)

(72) Inventors: John F. Zak, III, Chagrin Falls, OH (US); Jason R. Ertel, Twinsburg, OH (US); Sergey Makarov, Solon, OH (US); David J. Boll, Avon, OH (US); Alex Velet, Westlake, OH (US); Virginia Stewart, Cleveland Heights, OH (US)

(73) Assignee: TecTraum, Inc., Chagrin Falls, OH (US)

( * ) Notice: Subject to any disclaimer, the term of this patent is extended or adjusted under 35 U.S.C. 154(b) by 290 days.

(21) Appl. No.: 16/491,738

(22) PCT Filed: Mar. 9, 2018

(86) PCT No.: PCT/US2018/021752
§ 371 (c)(1),
(2) Date: Sep. 6, 2019

(87) PCT Pub. No.: WO2018/165552
PCT Pub. Date: Sep. 13, 2018

(65) Prior Publication Data
US 2021/0128345 A1 May 6, 2021

Related U.S. Application Data

(60) Provisional application No. 62/469,560, filed on Mar. 10, 2017.

(51) Int. Cl.
*A61F 7/00* (2006.01)

(52) U.S. Cl.
CPC .... *A61F 7/0085* (2013.01); *A61F 2007/0007* (2013.01); *A61F 2007/0009* (2013.01);
(Continued)

(58) Field of Classification Search
CPC ...... A61F 2007/0002; A61F 2007/0007; A61F 2007/0009; A61F 2007/0086;
(Continued)

(56) References Cited

U.S. PATENT DOCUMENTS 4,966,145 A * 10/1990 Kikumoto ............ A61G 5/1091
607/104
5,484,448 A 1/1996 Steele
(Continued)

FOREIGN PATENT DOCUMENTS

CN 103338730 10/2013
CN 203749679 8/2014
(Continued)

OTHER PUBLICATIONS

International Search Report filed in PCT/US18/21752 dated May 30, 2018.
(Continued)

*Primary Examiner* — Tigist S Demie
(74) *Attorney, Agent, or Firm* — Rankin, Hill & Clark LLP

(57) ABSTRACT

The system includes a pump, a heat exchanger, a bladder, a thermometer, and a controller. The heat exchanger is in fluid communication with the pump. The bladder is configured to be placed over a carotid artery, and is in fluid communication with the heat exchanger. The thermometer is located with respect to the heat exchanger and configured to measure a temperature of fluid downstream from the heat exchanger. The controller is in electrical communication 28 with the thermometer and the heat exchanger. The controller
(Continued)

is configured to 20 control power delivered to or flow through the heat exchanger such that the temperature of the fluid downstream from the heat exchanger measured by the thermometer is between 2 degrees C. and 10 degrees C. for between 10 minutes and 50 minutes.

16 Claims, 4 Drawing Sheets

(52) U.S. Cl.
CPC ............... *A61F 2007/0086* (2013.01); *A61F 2007/0096* (2013.01)

(58) Field of Classification Search
CPC ...... A61F 2007/0096; A61F 2007/0231; A61F 7/0085; A61F 7/02
See application file for complete search history.

(56) References Cited

U.S. PATENT DOCUMENTS

| | | | |
|---|---|---|---|
| 5,755,755 A | 5/1998 | Panyard | |
| 5,871,526 A | 2/1999 | Gibbs et al. | |
| 6,156,059 A | 12/2000 | Olofsson | |
| 6,312,453 B1 | 11/2001 | Stefanile | |
| 6,511,502 B2 | 1/2003 | Fletcher | |
| 7,846,118 B2 | 12/2010 | Sandhu | |
| 7,892,269 B2 | 2/2011 | Collins et al. | |
| 7,896,910 B2 | 3/2011 | Schirrmacher | |
| 8,425,583 B2 | 4/2013 | Nofzinger | |
| 8,454,671 B2 | 6/2013 | Lennox | |
| 8,491,644 B1 | 7/2013 | Carson | |
| 8,900,170 B1 | 12/2014 | Elkins | |
| 2002/0103520 A1 | 8/2002 | Latham | |
| 2004/0133135 A1 | 7/2004 | Diana | |
| 2004/0249427 A1* | 12/2004 | Nabilsi | A61F 7/0085 607/104 |
| 2009/0240312 A1* | 9/2009 | Koewler | A61F 7/02 607/104 |
| 2011/0040223 A1* | 2/2011 | Sandhu | A61F 5/055 602/14 |
| 2011/0295163 A1 | 12/2011 | Vijayanagar | |
| 2012/0143110 A1 | 6/2012 | Maher | |
| 2012/0289757 A1 | 11/2012 | Boyden | |
| 2013/0138185 A1 | 5/2013 | Paxman | |
| 2014/0046411 A1 | 2/2014 | Elkins | |
| 2016/0354232 A1 | 12/2016 | Rosental | |

FOREIGN PATENT DOCUMENTS

| | | |
|---|---|---|
| JP | 2006288568 | 10/2006 |
| WO | 03/030790 | 4/2003 |
| WO | 2012/028730 | 3/2012 |
| WO | 2015/180804 | 12/2015 |
| WO | 2015180804 | 12/2015 |
| WO | 2016/016610 | 2/2016 |
| WO | 2016/025082 | 2/2016 |

OTHER PUBLICATIONS

Supplementary EP Search Report filed in EP 18 76 4625 dated Feb. 1, 2021.

\* cited by examiner

SYSTEM AND METHOD FOR TREATING BRAIN INJURY

BACKGROUND

U.S. Pat. No. 6,183,501 B1 discloses a cooling system having a head and neck device which can be cooled to reduce trauma to the brain. The head device includes panels that each house a cold element to facilitate cooling. The head device secures to the head of an individual and covers over the individual's carotid arteries, which provide blood to the brain.

Comfort issues arise when an individual wears such a head cooling device. Many individuals are familiar with the discomfort resulting from the quick consumption of cold beverages or foods such as ice cream. Wearers of the aforementioned head cooling device can experience similar discomfort. If wearers of these head cooling devices experience too much discomfort, they may cut short the time duration that they wear the head cooling device. Shortening the treatment time below a particular minimum time threshold may decrease the efficacy of the treatment for reducing trauma to the brain.

SUMMARY

In view of the foregoing, a method for treating a brain injury includes pumping fluid through a heat exchanger to a bladder placed on a wearer's neck adjacent to or over a carotid artery. The method further includes removing heat from the fluid as the fluid passes through the heat exchanger, and measuring a temperature of the fluid downstream from the heat exchanger. The method also includes controlling at least one of power delivered to the heat exchanger and flow of fluid through the heat exchanger such that the measured temperature of the fluid downstream from the heat exchanger is between 2 degrees C. and 10 degrees C. for between 10 minutes and 50 minutes.

A system for treating a brain injury includes a pump, a heat exchanger, a bladder, a thermometer, and a controller. The heat exchanger is in fluid communication with the pump. The bladder is configured to be placed over a carotid artery, and is in fluid communication with the heat exchanger. The thermometer is located with respect to the heat exchanger and configured to measure a temperature of fluid downstream from the heat exchanger. The controller is in electrical communication with the thermometer and the heat exchanger. The controller is configured to control power delivered to or flow through the heat exchanger such that the temperature of the fluid downstream from the heat exchanger measured by the thermometer is between 2 degrees C. and 10 degrees C. for between 10 minutes and 50 minutes.

DETAILED DESCRIPTION

Figure 1:
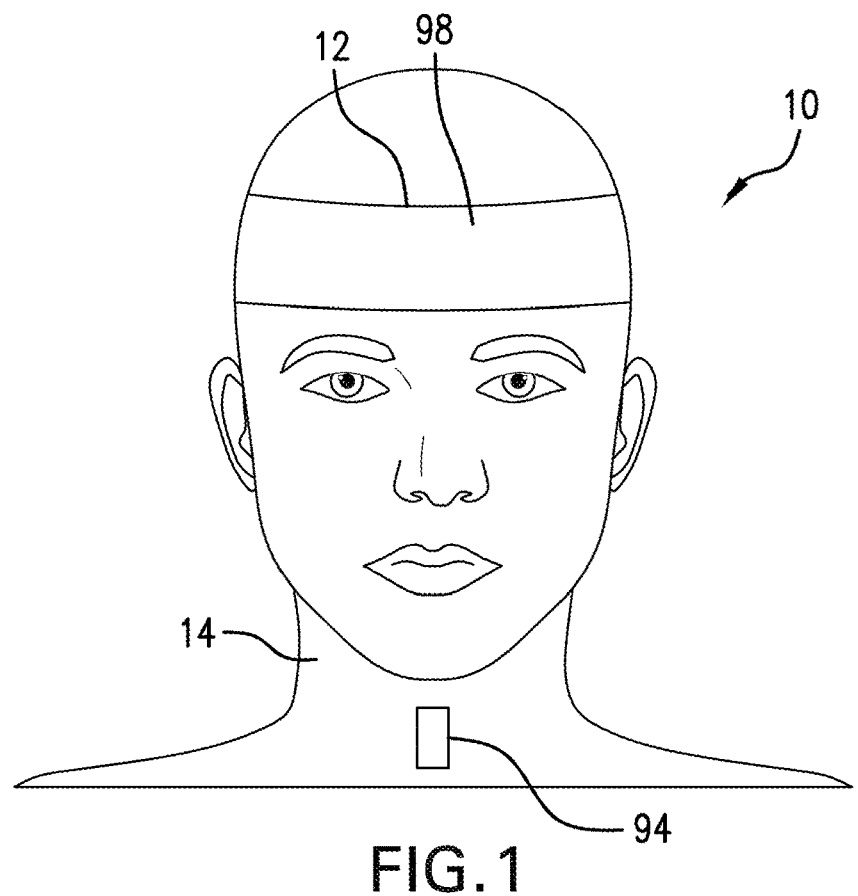
FIG. 1 is a schematic depiction of the head and neck of a human.
Figure 2:
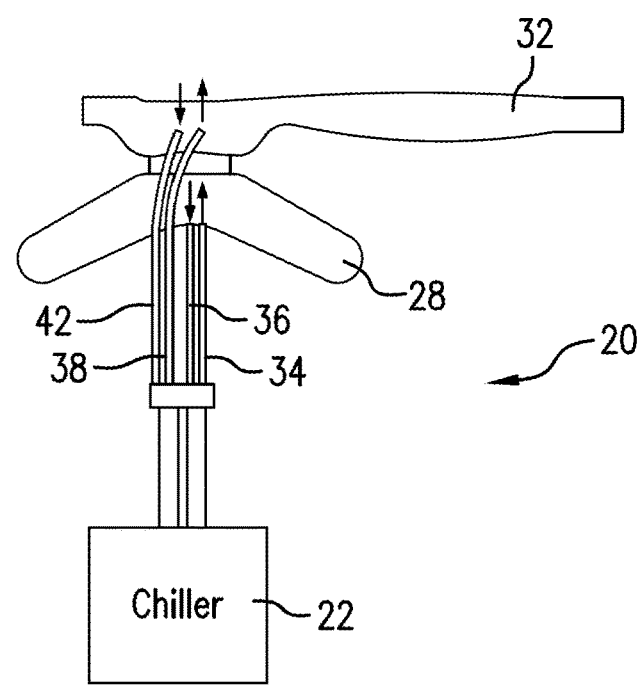
FIG. 2 is a schematic depiction of a system for treating a brain injury.

FIG. 1 depicts a person's head 10 having a forehead region 12 and supported by a neck 14. FIG. 2 depicts a system 20 that is useful in treating a brain injury. The system 20 generally includes a chiller unit 22 connected with bladders 24, 26 (FIG. 3) carried by respective carriers 28, 32 via fluid lines 34, 36, 38, 42, respectively.

Figure 3:
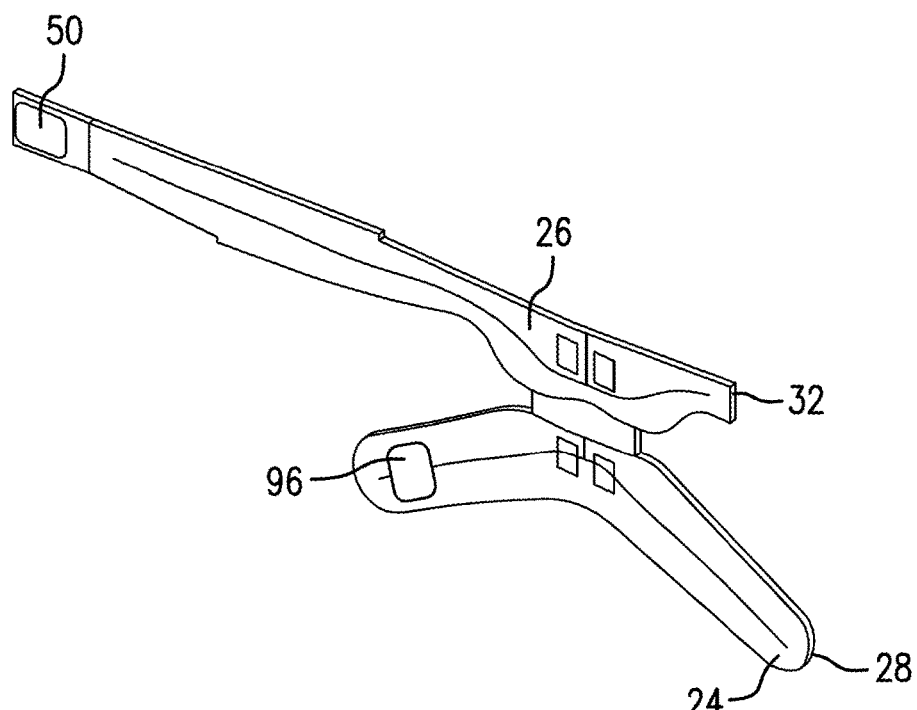
FIG. 3 is a perspective view of bladders and carriers of the system depicted in FIG. 2.

Carotid arteries run through the neck 14 to provide blood to the brain. With reference to FIG. 3, the lower bladder 24 is configured to be placed around the neck 14 and over the carotid arteries. Also, the upper bladder 26 can be wrapped around the forehead region 12. The bladders 24, 26 can be retained around the neck 14 and forehead region 12 using hook and loop fasteners 50, only one example of which is shown in FIG. 3. Cool fluid from the chiller unit 22 is pumped to the bladders 24, 26 to cool blood flowing through the carotid arteries in a manner that provides brain cooling and to also cool the forehead region 12.

Figure 5:
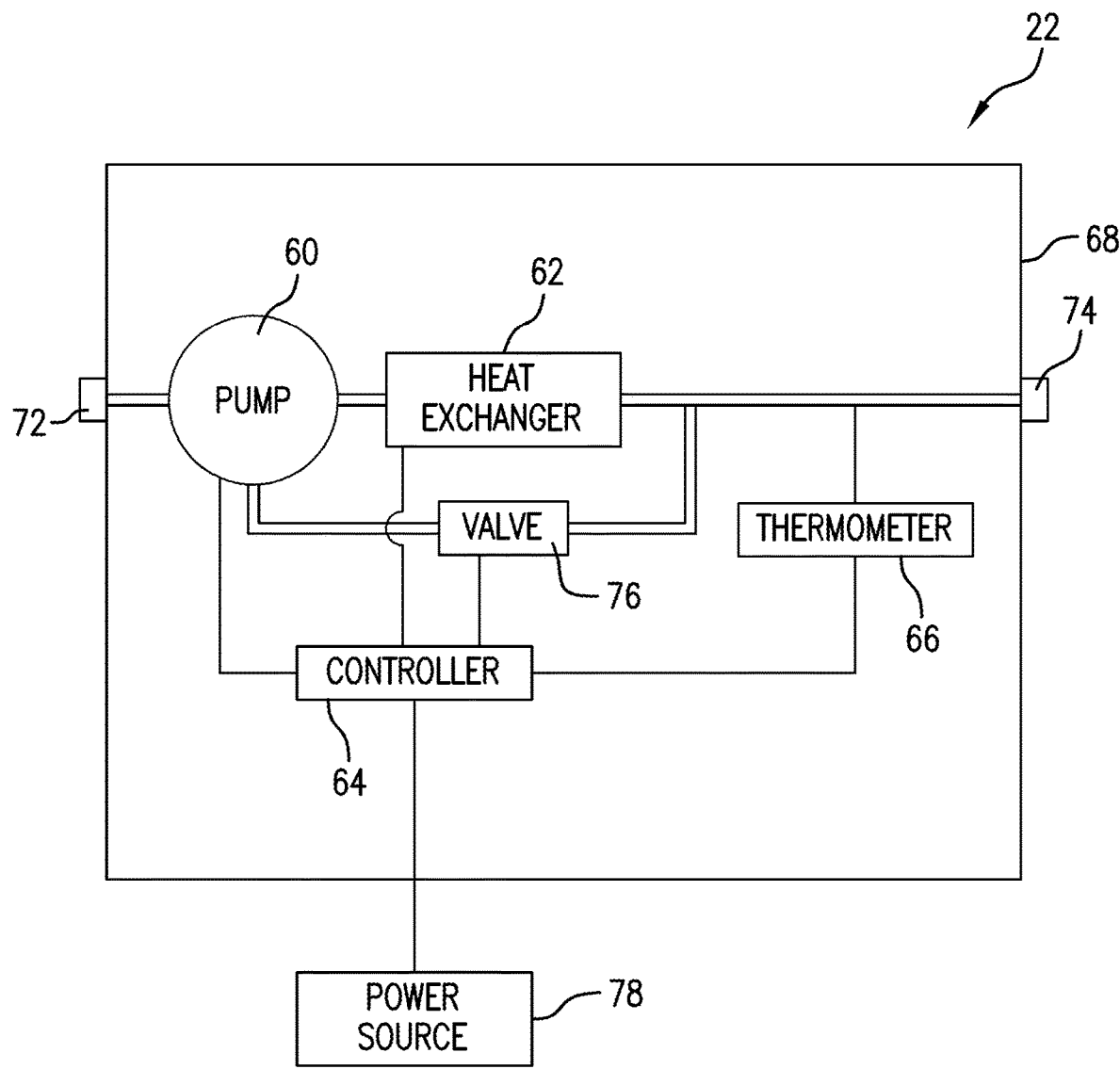
FIG. 5 is a schematic depiction of a chiller unit of the system depicted in FIG. 2.

FIG. 5 schematically depicts the chiller unit 22. The chiller unit 22 includes a pump 60, a heat exchanger 62, a controller 64, and a thermometer 66. The pump 60, the heat exchanger 62, the controller 64, and the thermometer 66 are disposed in a casing 68, which is schematically depicted in FIG. 5. The chiller unit 22 includes a chiller inlet 72, which receives relatively warmer water from the bladders 24, 26. The pump 60 moves the fluid incoming from the chiller inlet 72 through the heat exchanger 62 where the fluid can be cooled to a desired temperature and then pumped through a chiller outlet 74 back toward the bladders 24, 26. If desired, the heat exchanger 62 can be operated to heat fluid. The chiller unit 22 can also include a valve 76, which can allow fluid from the pump 60 to bypass the heat exchanger 62. The chiller unit 22 in the illustrated embodiment receives power from an external power source 78, which can provide power to each of the components of the chiller unit 22. The power source 78 could also be located within the casing 68, for example when the power source is a battery or battery pack. The chiller unit 22 can also include a display and a user interface, which are not shown, to allow an operator to operate the chiller unit 22.

A method for treating a brain injury will be described in detail with regard to the system 20 depicted in FIG. 2. Nevertheless, the method for treating a brain injury could be used with other types of systems capable of performing the operations described below. The method includes pumping fluid through the heat exchanger 62 (FIG. 5) to the lower bladder 24 placed on a person's neck adjacent to or over a carotid artery. Heat is removed from the fluid as the fluid passes through the heat exchanger 62. The thermometer 66 measures the temperature of the fluid exiting the heat exchanger 62. Power delivered to the heat exchanger 62, from the external power source 78 for example, can be controlled or flow through the heat exchanger 62 can be controlled by the controller 64 such that the measured temperature of the fluid downstream from the heat exchanger 62 is between 2° C. and 10° C. for between 10 minutes and 50 minutes. More particularly, power delivered to the heat exchanger 62 or flow through the heat exchanger 62 can be controlled by the controller 64 such that the temperature of the fluid downstream from the heat exchanger 62 is between 4° C. and 8° C. for between about 20 minutes and 40 minutes. More particularly, power delivered to the heat exchanger 62 or flow through the heat exchanger 62 can be controlled by the controller 64 such that the measured temperature of the fluid downstream from the heat exchanger 62 is about 6° C. for about 30 minutes.

The thermometer 66 can measure the temperature of the fluid exiting the heat exchanger 62 prior to the fluid exiting the casing 68 and entering the fluid lines 34, 38 respectively. The thermometer 66 communicates with the controller 64 to provide the controller the measured temperature of the fluid exiting the heat exchanger 62. Based on the measured temperature, the controller 64 can adjust the power, for example by using pulse width modulation (PWM), delivered to the heat exchanger 62. More power can be delivered to the cooling side of the heat exchanger 62 when the measured temperature is higher than the desired temperature. In addition or alternatively to controlling power to the heat exchanger 62, the controller 64 can open and close the valve 76. For example, the valve 76 can be opened and fluid allowed to bypass the heat exchanger 62 in route to the chiller outlet 74 when the measured temperature is lower than a desired temperature. By way of example, when the thermometer 66 measures the temperature of the fluid exiting the heat exchanger as too cold (based on a predetermined threshold), then the controller 64 can open the valve 76 to allow relatively warmer fluid from upstream of the heat exchanger 62 to bypass the heat exchanger to raise the temperature of the fluid being delivered to the chiller outlet 74. Alternatively, the flow rate of the pump 60 can be adjusted, e.g., lowered, so that less fluid is delivered to the heat exchanger 62 when the measured temperature is lower than the desired temperature.

Figure 4:
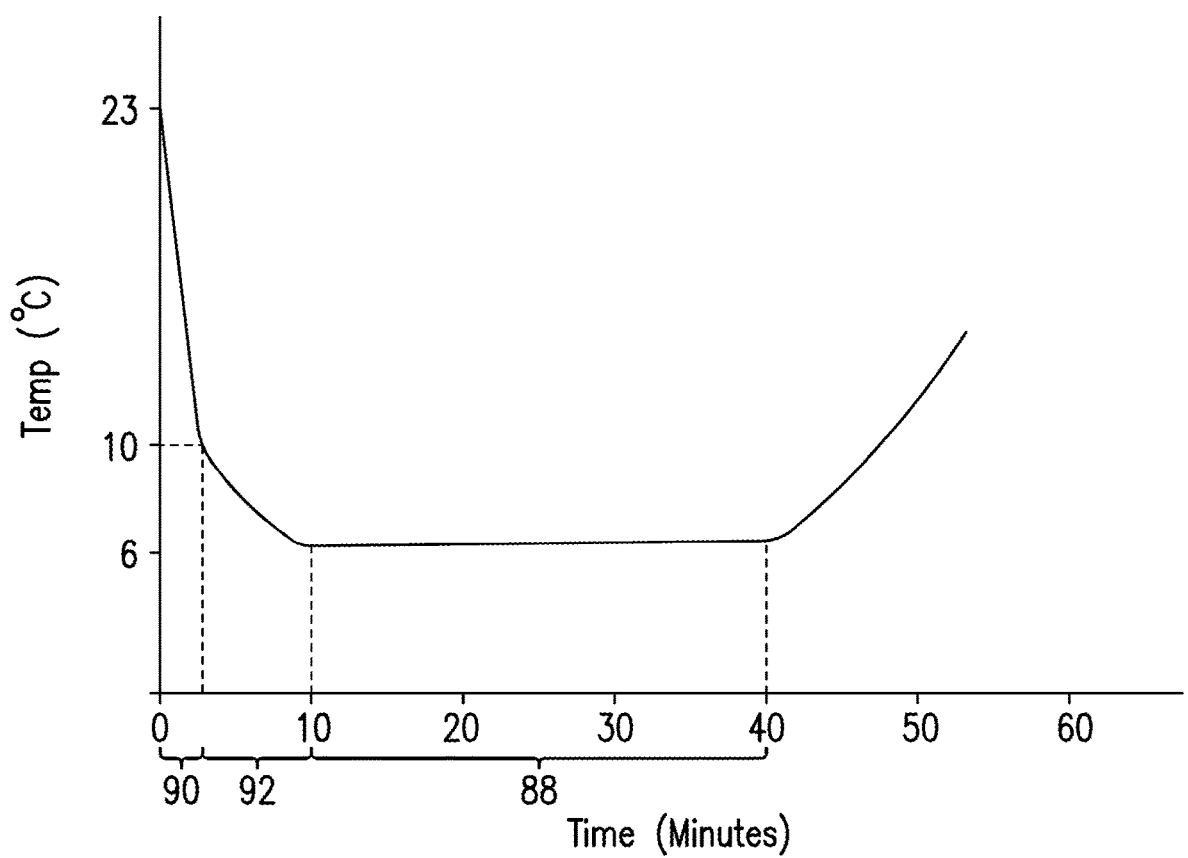
FIG. 4 is a graph depicting temperature versus time for fluid in the system depicted in FIG. 2.

FIG. 4 depicts a particular example of the temperature of the fluid downstream from the heat exchanger 62 as compared to time for a particular treatment cycle. FIG. 4 is just one example and should not be found to limit the invention, which is defined by the claims. Power delivered to or flow through the heat exchanger 62 can be controlled such that the measured temperature of the fluid exiting the heat exchanger 62 is a treatment temperature (which is 6° C. in FIG. 4) between 2° C. and 10° C. for a desired treatment time period 88. An initial rate of change of temperature from an initial temperature (which is 23° C. in FIG. 4) toward the treatment temperature is faster during an initial ramp down time period 90 from the initial temperature to a first predetermined temperature threshold (which is 10° C. in FIG. 4) as compared to a secondary ramp down time period 92 from the first predetermined temperature threshold to the treatment temperature. As can be seen in FIG. 4, the slope of the curve from the initial temperature (23° C. in FIG. 4) to the first predetermined temperature threshold (10° C. in FIG. 4) is much steeper than the slope of the curve from the first predetermined temperature threshold (10° C. in FIG. 4) to the treatment temperature (6° C. in FIG. 4). This provides initial cooling to the wearer of the bladders 24, 26 during the initial ramp down time period 90, and provides a longer acclimation time from the first predetermined temperature threshold to the treatment temperature. When the treatment temperature is relatively much colder than ambient temperature, some wearers of the bladders 24, 26 may experience discomfort when the temperature of the fluid within the bladder is brought to the treatment temperature in a very short amount of time. Providing a longer and/or a type of step-wise acclimation period including the initial ramp down time period 90 and the secondary ramp down time period 92 mitigates the discomfort that may be felt by the wearer of the bladders 24, 26. Power delivered to or flow through the heat exchanger 62 can be further controlled such that the initial ramp down time period 90 added to the secondary ramp down time period 92 is less than 10 minutes. This allows an adequate amount of time for the wearer to wear the bladders 24, 26 at the treatment temperature, which is 6° C. in FIG. 4, so that the overall treatment period (the ramp down time periods 90, 92 added to the treatment time period 88) is not too long. If desired, the initial ramp down time period 90 added to the secondary ramp down time period 92 can be less than 15 minutes or less than 5 minutes.

FIG. 4 depicts the initial ramp down time period 90 and the secondary ramp down time period 92. A single ramp down period having a predetermined slope or more than two ramp down periods having different slopes could be provided. The time period that it takes the fluid temperature downstream from the heat exchanger 62, which is measured by the thermometer 66, to decrease from the initial temperature to the treatment temperature can be referred to as the overall ramp down time period. It is desirable to have the overall ramp down period be less than 15 minutes, and preferably less than 10 minutes. It is also desirable to have the overall ramp down time period added to the treatment time period to be less than 90 minutes, and preferably less than 40 minutes. If the wearer of the bladders 24, 26 must wear them for too long, then adherence to the protocol is less likely.

Figure 6:
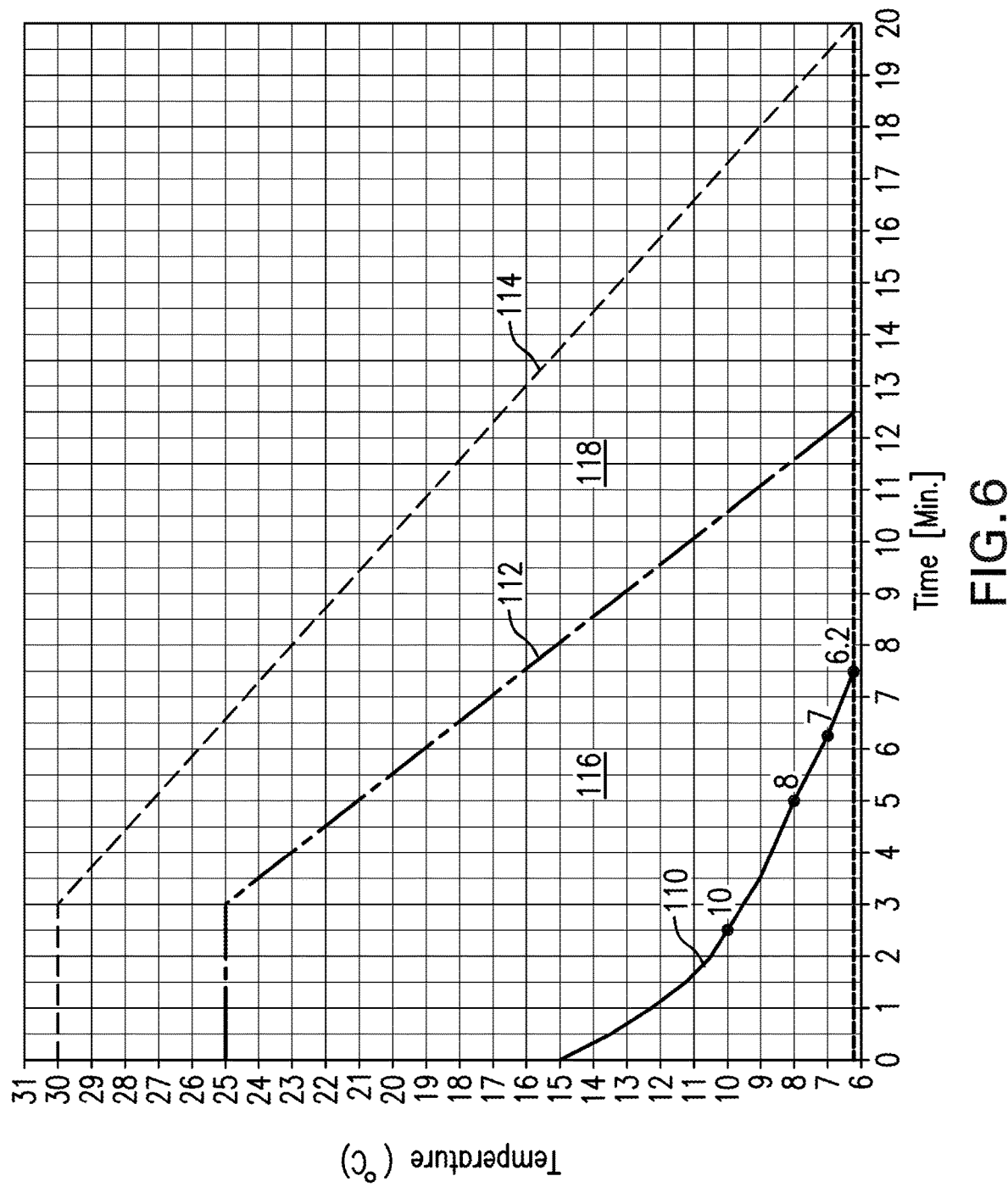
FIG. 6 is another graph depicting temperature versus time showing boundaries for an overall ramp down time period curve.

FIG. 6 depicts three curves, or lines: a lower ramp down boundary 110, a first upper ramp down boundary 112 and a second upper ramp down boundary 114. A lower working zone 116 is defined as an area between the lower ramp down boundary 110 and the first upper ramp down boundary 112. An upper working zone 118 is defined as an area between the first upper ramp down boundary 112 and the second upper ramp down boundary 114.

When the initial temperature for fluid in the system 20 is between 15° C. and 25° C., which is typically a function of the ambient temperature, it is desirable to operate the chiller unit 22 in a manner so that the overall ramp down time period (similar to the initial ramp down time period 90 added to the secondary ramp down time period 92 shown in FIG. 4) is not too long, and the temperature decrease over time follows a line or curve from the starting temperature to the treatment temperature (about 6° C. in FIG. 6) that is within the lower working zone 116, i.e., bounded by the lower ramp down boundary 110 and the first upper ramp down boundary 112. The controller 64 controls power delivered to or flow through the heat exchanger 62 so that the overall ramp down time period is between about 7 minutes and about 13 minutes, as seen in FIG. 6, when the initial temperature is less than 25 degrees C. and greater 15 degrees C. The controller 64 also controls the rate of change of temperature over time to maintain a line or curve between the lower ramp down boundary 110 and the first upper ramp down boundary 112 from the initial temperature to the treatment temperature. With reference to FIG. 6, the controller 64 can control at least one of the pump 60, the heat exchanger 62 and the valve 76 such that the overall ramp down period time is less than 13 minutes when the initial temperature is less than 25° C. and the overall ramp down period time is less than 8 minutes when the initial temperature is less than 25° C. and greater 15° C.

The lower ramp down boundary 110 follows a similar path as the portion of the curve depicted in FIG. 4 for the initial ramp down time period 90 added to the secondary ramp down time period 92. In FIG. 6, the slope of the curve for the lower ramp down boundary 110 from 15° C. to the first predetermined temperature threshold (10° C. in FIG. 6) is steeper than the slope of the curve from the first predetermined temperature threshold (10° C. in FIG. 6) to the treatment temperature (about 6° C. in FIG. 6). The first upper ramp down boundary 112 follows a horizontal line at 25° C. from 0 to 3 minutes. This horizontal line at 25° C. from 0 to 3 minutes is to avoid a peak draw on the power source 78 (FIG. 5) that could trip electrical hardware in the chiller unit 22. The allows the chiller unit 22 to slowly start cooling when power demand is highest and ease into a ramp down period when the initial temperature is at 25° C. If the horizontal line at 25° C. from 0 to 3 minutes in the first upper ramp down boundary 112 was not provided, then a larger power supply to avoid edge case scenarios that could trip the power source and other electrical hardware in the chiller unit 22 may be necessary, which could impact the cost of the chiller unit 22.

With continued reference to FIG. 6, when the initial temperature for fluid in the system 20 is greater than 25° C. it will take longer to ramp down to the treatment temperature. This allows the chiller unit 22 to slowly start cooling when power demand is highest and ease into a ramp down period when the initial temperature is greater than 25° C. The controller 64 controls power delivered to or flow through the heat exchanger 62 so that the overall ramp down time period is less than 21 minutes, when the initial temperature is greater than 25 degrees C. and less than 30 degrees C. The controller 64 also controls the rate of change of temperature over time to maintain a line or curve between the first upper ramp down boundary 112 and the second upper ramp down boundary 114 from the initial temperature to the treatment temperature.

With reference back to FIG. 4, power delivered to or flow through the heat exchanger 62 can also be controlled such that the measured temperature of the fluid downstream from the heat exchanger 62 is a treatment temperature (6° C. in FIG. 4) between 2° C. and 10° C. during a time period over which the fluid downstream from the heat exchanger 62 is at the treatment temperature for the treatment time period 88 between 10 minutes and 50 minutes. The treatment time period 88 in FIG. 4 is 30 minutes. To aid in acclimation, the slope of the curve for the time period immediately or nearly immediately preceding the treatment time period 88, which is the secondary ramp down time period 92 in FIG. 4, can be less steep than earlier time periods, e.g. the initial ramp down time period 90 in FIG. 4.

Power delivered to the heat exchanger 62 (FIG. 5) can be controlled such that power is no longer delivered or power is delivered to heat fluid passing through the heat exchanger 62 after the treatment time period has elapsed. Fluid delivery can also be controlled, e.g., the valve 76 can be opened, such that fluid is allowed to bypass the heat exchanger 62 after the treatment time period has elapsed. Power delivered to the heat exchanger 62 can be controlled such that power is no longer delivered or power is delivered to heat fluid passing through the heat exchanger 62 after the treatment time period has elapsed until the measured temperature equals at least 20° C., so that adequate acclimation can be provided to the next wearer of the bladders 24, 26. Also, fluid delivery can also be controlled to the heat exchanger 62 after the treatment time period has elapsed until the measured temperature equals at least 20° C., so that adequate acclimation can be provided to the next wearer of the bladders 24, 26.

With reference back to FIG. 1, the area around the thyroid cartilage on the wearer's neck 14 can be particularly sensitive. A barrier can be provided to reduce thermal conductivity in this area. For example, an insulating material 94 can be affixed on the skin over the thyroid cartilage prior to placement of the lower bladder 24 over the carotid artery.

Alternatively, a protective barrier 96 can be applied over the lower bladder 24, and the protective barrier could connect with the lower bladder 24 or the lower carrier 28. With continued reference to FIG. 1, an insulating cap or headband 98 could also be placed around the forehead region 12 prior to placement of the upper bladder 26 around the forehead. Also, different types of insulating barriers could be applied to the forehead region 12 instead of the headband 98. It can be desirable to pump fluid from the chiller unit 22 to both the upper bladder 26 and the lower bladder 24 at the same temperature. It has also been found, however, that wearers of the bladders 24, 26 are able to tolerate colder temperatures around the neck 14 as compared to around the forehead region 12. Since it is desirable to cool the area around the carotid artery as much as possible, since the carotid arteries provide blood to the brain, providing insulative material on the forehead region 12 can allow very cold fluid, e.g., about 6° C., to be pumped from the chiller unit 22 to both bladders 24, 26, and the insulative material in the forehead region 12 can provide some relief to the wearer while more cooling can take place at the neck 14.

A method and system for treating a brain injury has been described above with particularity. Modifications and alterations will occur to those upon reading and understanding the preceding detailed description. The invention, however, is not limited to only the system described above. Instead, the invention is broadly defined by the appended claims and the equivalents thereof. Also, various presently unforeseen or unanticipated alternatives, modifications, variations or improvements may be subsequently made by those skilled in the art which are also intended to be encompassed by the following claims.

The invention claimed is:

1. A method for treating a brain injury, comprising:
pumping fluid through a heat exchanger to a bladder placed on a wearer's neck adjacent to or over a carotid artery;
removing heat from the fluid passing through the heat exchanger;
measuring a temperature of fluid downstream from the heat exchanger; and
controlling at least one of power delivered to the heat exchanger and flow of the fluid through the heat exchanger by opening and closing a valve to allow fluid from a pump to bypass the heat exchanger such that the measured temperature of the fluid downstream from the heat exchanger is a treatment temperature between 2 degrees C. and 10 degrees C. for between 10 minutes and 50 minutes, and a rate of change of temperature from an initial temperature toward the treatment temperature is faster during an earlier ramp down period from an initial temperature toward a first predetermined temperature threshold as compared to a later ramp down period from the first predetermined temperature threshold to the treatment temperature.

2. The method of claim 1, wherein the pump, the heat exchanger, and a thermometer for measuring the temperature are positioned in a casing and the bladder is connected with the casing with fluid lines, wherein measuring the temperature of the fluid downstream from the heat exchanger further includes measuring the temperature prior to the fluid exiting the casing and entering the fluid lines.

3. The method of claim 1, wherein controlling at least one of power delivered to the heat exchanger and flow of fluid through the heat exchanger further includes:
controlling power delivered to or flow through the heat exchanger such that an overall ramp down period time from the initial temperature to the treatment temperature is less than 15 minutes.

4. The method of claim 3, wherein controlling at least one of power delivered to the heat exchanger and flow of fluid through the heat exchanger further includes:

controlling power delivered to or flow through the heat exchanger such that the overall ramp down period time is less than 21 minutes when the initial temperature is less than 30 degrees C. and greater than 25 degrees C., and the overall ramp down period time is less than 13 minutes when the initial temperature is less than 25 degrees C. and greater 15 degrees C.

5. The method of claim 1, wherein controlling at least one of power delivered to the heat exchanger and flow of fluid through the heat exchanger further includes:

controlling power delivered to or flow through the heat exchanger such that a time period over which the fluid downstream from the heat exchanger is at the treatment temperature is a treatment time period between 10 minutes and 50 minutes.

6. The method of claim 5, wherein controlling at least one of power delivered to the heat exchanger and flow of fluid through the heat exchanger further includes:

controlling power delivered to the heat exchanger such that power is no longer delivered or power is delivered to heat fluid passing through the heat exchanger after the treatment time period has elapsed.

7. The method of claim 6, wherein controlling at least one of power delivered to the heat exchanger and flow of fluid through the heat exchanger further includes:

controlling power delivered to the heat exchanger such that power is no longer delivered or power is delivered to heat fluid passing through the heat exchanger after the treatment time has elapsed until the measured temperature equals at least 20 degrees C.

8. The method of claim 1, wherein controlling at least one of power delivered to the heat exchanger and flow of fluid through the heat exchanger further includes:

controlling flow through the heat exchanger after the treatment time has elapsed until the measured temperature equals at least 20 degrees C.

9. The method of claim 1, further comprising providing an insulating material on skin over or adjacent to the thyroid cartilage prior to pumping fluid through the heat exchanger to the bladder placed on the wearer's neck.

10. The method of claim 1, further comprising providing an insulating material on the wearer's forehead region, and pumping additional fluid to a second bladder placed on the wearer's forehead after providing the insulating material on the wearer's forehead region, wherein the temperature of the fluid delivered to the bladder placed on the wearer's neck is equal to the temperature of the additional fluid delivered to the second bladder placed on the wearer's forehead region.

11. A system for treating a brain injury, comprising:
a pump;
a heat exchanger in fluid communication with the pump;
a valve, which can allow fluid from the pump to bypass the heat exchanger;
a bladder configured to be placed over a carotid artery, the bladder being in fluid communication with the heat exchanger;
a thermometer located with respect to the heat exchanger and configured to measure a temperature of fluid downstream from the heat exchanger; and
a controller in electrical communication with the thermometer, the valve and the heat exchanger, the controller configured to control power delivered to the heat exchanger and to control the valve to control flow of fluid through the heat exchanger such that the temperature of the fluid downstream from the heat exchanger measured by the thermometer is a treatment temperature between 2 degrees C. and 10 degrees C. for between 10 minutes and 50 minutes,
wherein the controller is configured to control power delivered to or flow through the heat exchanger such that a rate of change of temperature from an initial temperature toward the treatment temperature is faster during an earlier ramp down period from the initial temperature toward a first predetermined temperature threshold as compared to a later ramp down period from the first predetermined temperature threshold to the treatment temperature,
wherein the controller is configured to control power delivered to or flow through the heat exchanger such that the overall ramp down period time is greater than 3 minutes and less than 13 minutes when the initial temperature is less than 25 degrees C. and the overall ramp down period time is greater than 3 minutes and less than 8 minutes when the initial temperature is less than 25 degrees C. and greater 15 degrees C.

12. The system of claim 11, further comprising a casing, wherein the pump, the heat exchanger, and the thermometer are positioned in the casing and the bladder is connected with the casing with fluid lines.

13. The system of claim 11, wherein the controller is configured to control power delivered to the heat exchanger such that power is no longer delivered or power is delivered to heat fluid passing through the heat exchanger after the treatment time period has elapsed.

14. The system of claim 13, wherein the controller is configured to control power delivered to the heat exchanger such that power is no longer delivered or power is delivered to heat fluid passing through the heat exchanger after the treatment time has elapsed until the measured temperature equals at least 20 degrees C.

15. The system of claim 11, further comprising an insulating material for placing on skin over thyroid cartilage.

16. The system of claim 11, further comprising an insulating material for placing on skin over a forehead region.

* * * * *